(12) United States Patent
Kempf et al.

(10) Patent No.: US 8,901,157 B2
(45) Date of Patent: Dec. 2, 2014

(54) COMPOSITIONS AND METHODS OF USE OF RITONAVIR FOR TREATING HCV

(75) Inventors: Dale J. Kempf, Libertyville, IL (US); Kennan C. Marsh, Lake Forest, IL (US)

(73) Assignee: AbbVie Inc., North Chicago, IL (US)

( * ) Notice: Subject to any disclaimer, the term of this patent is extended or adjusted under 35 U.S.C. 154(b) by 750 days.

(21) Appl. No.: 12/958,899

(22) Filed: Dec. 2, 2010

(65) Prior Publication Data

US 2011/0091423 A1 Apr. 21, 2011

Related U.S. Application Data

(63) Continuation of application No. 11/682,668, filed on Mar. 6, 2007, now abandoned.

(60) Provisional application No. 60/779,501, filed on Mar. 6, 2006.

(51) Int. Cl.
*A61K 31/407* (2006.01)
*A61K 31/4965* (2006.01)
*A61K 31/497* (2006.01)
*A61K 38/21* (2006.01)
*A61K 31/403* (2006.01)
*A61K 31/7056* (2006.01)

(52) U.S. Cl.
CPC ............. *A61K 38/212* (2013.01); *A61K 31/407* (2013.01); *A61K 31/497* (2013.01); *A61K 31/4965* (2013.01); *A61K 31/7056* (2013.01)
USPC ........... 514/365; 514/366; 514/408; 514/412; 424/85.4; 548/151; 548/416; 548/452

(58) Field of Classification Search
USPC ................ 424/85.4; 514/365, 366, 408, 412; 548/151, 416, 452
See application file for complete search history.

(56) References Cited

U.S. PATENT DOCUMENTS

| | | | |
|---|---|---|---|
| 5,541,206 A | 7/1996 | Kempf et al. | |
| 5,674,882 A | 10/1997 | Kempf et al. | |
| 5,830,905 A * | 11/1998 | Diana et al. | 514/322 |
| 5,886,036 A | 3/1999 | Kempf et al. | |
| 6,037,157 A | 3/2000 | Norbeck et al. | |
| 6,703,403 B2 | 3/2004 | Norbeck et al. | |
| 2003/0216325 A1 | 11/2003 | Saksena et al. | |
| 2005/0249702 A1 | 11/2005 | Njoroge et al. | |
| 2006/0003942 A1 | 1/2006 | Tung et al. | |
| 2008/0267915 A1 | 10/2008 | Lin et al. | |

FOREIGN PATENT DOCUMENTS

| | | |
|---|---|---|
| WO | WO9414436 A1 | 7/1994 |
| WO | WO0218369 A2 | 3/2002 |
| WO | WO2005042020 A2 | 5/2005 |
| WO | WO2005123076 A2 | 12/2005 |

OTHER PUBLICATIONS

International Search Report from WO2007/103934 dated Sep. 2, 2008.
McHutchison J.G., et al., "The Face of Future Hepatitis C Antiviral Drug Development: Recent Biological and Virologic Advances and Their Translation to Drug Development and Clinical Practice," Journal of Hepatology, 2006, vol. 44 (2), pp. 411-421.
Supplementary European Search Report Application No. EP07758000, mailed on Oct. 12, 2010, 3 pages.
Zeldin, et al., "Pharmacological and therapeutic properties of ritonavir-boosted protease inhibitor therapy in HIV-infected patients," Journal of Antimicrobial Chemotherapy, 2004, vol. 53, pp. 4-9.
Written Opinion for Application No. PCT/US2007/63408, mailed on Sep. 2, 2008, 16 pages.

* cited by examiner

*Primary Examiner* — Sreeni Padmanabhan
*Assistant Examiner* — Sahar Javanmard
(74) *Attorney, Agent, or Firm* — Lisa V. Mueller; Michael Best & Friedrich LLP

(57) ABSTRACT

The present invention discloses compositions and a method of improving the pharmacokinetics of pharmaceutical agents (or pharmaceutically acceptable salts, esters, and prodrugs thereof) which are metabolized by cytochrome P450 monoxygenase comprising coadministering ritonavir or a pharmaceutically acceptable salt, ester, and prodrug thereof.

5 Claims, 3 Drawing Sheets

Figure 1

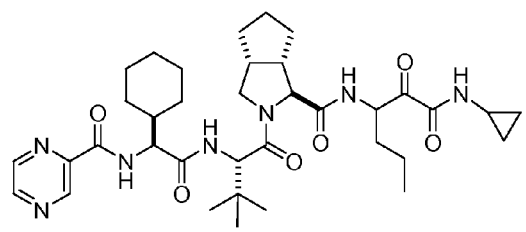

VX-950

2-(2-{2-Cyclohexyl-2-[(pyrazine-2-carbonyl)-amino]-acetylamino}-3,3-dimethyl-butyryl)-octahydro-cyclopenta[c]pyrrole-1-carboxylic acid (1-cyclopropylaminooxalyl-butyl)-amide

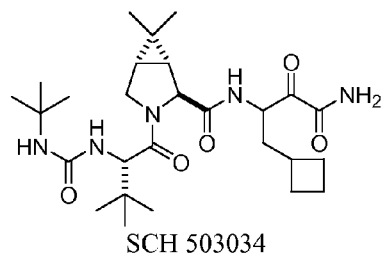

SCH 503034

(2 - Oxo - 3 - (cyclobutylmethyl)) propyl) amide, 3 - ((tert - butyloxycarbonyl) - 2 - tert - butylglycyl - (1,1 - dimethylcyclopropan (2,3 - c) prolin - 2 - yl)) amino -, 3-[2-(3-*tert*-Butyl-ureido)-3,3-dimethyl-butyryl]-6,6-dimethyl-3-aza-bicyclo[3.1.0]hexane-2-carboxylic acid (2-carbamoyl-1-cyclobutylmethyl-2-oxo-ethyl)-amide

COMPOSITIONS AND METHODS OF USE OF RITONAVIR FOR TREATING HCV

CROSS-REFERENCE TO RELATED APPLICATIONS

This is a continuation application of U.S. patent application Ser. No. 11/682,668, filed on Mar. 6, 2007, which claims the benefit of U.S. Provisional Application No. 60/779,501, filed on Mar. 6, 2006, the contents of all of which are hereby incorporated by reference.

BACKGROUND OF THE INVENTION

Hepatitis C is a blood-borne disease that infects approximately 150-200 million individuals worldwide. Hepatitis C is a viral disease that is caused by a hepatropic virus, HCV (Hepatitis C Virus). Infection with HCV results in liver inflammation which can ultimately result in cirrhosis and liver cancer. Although many individuals do not exhibit symptoms related to hepatitis C infection, it is the leading cause of liver transplants in the United States.

Although science was aware of the hepatitis A and B viruses for decades, it was not until the late 1980s that discovery of hepatitis C virus was published for the medical and scientific communities. The discovery confirmed that most post-transfusion hepatitis cases were not due to hepatitis A and B viruses, but instead were due to the newly discovered hepatitis C virus. With the discovery of the hepatitis C virus, the need arose for methods to treat the virus and to understand the urstructural and replication process performed by the virus.

HCV is a small, enveloped, single stranded, positive sense RNA virus in the family Flaviviridae. HCV mainly replicates within hepatocytes. HCV particles bind to receptors on the surfaces of hepatocytes and subsequently enter the cells. The RNA genome encodes a single stranded polypeptide comprising of approximately 3000 amino acids.

Therapies for Hepatitis C Virus (HCV)

Several different types of HCV therapies exist. One of the most common therapies involves using the combination of alpha-interferon and ribavirin. Even with this type of therapy many patients do not exhibit a reduction in viral activity. Accordingly, there is a clear long-felt and unresolved need to develop new effective therapeutics in the treatment of HCV infection.

The inventors have herein developed compositions and methods of improving the pharmacokinetics of HCV pharmaceutical agents (or pharmaceutically acceptable salts, esters, and prodrugs thereof) which are metabolized by cytochrome P450 monoxygenase comprising coadministering ritonavir or a pharmaceutically acceptable salt, ester, and prodrug thereof with such HCV compounds.

SUMMARY OF THE INVENTION

In accordance with the present invention, there is disclosed compositions and a method of improving the pharmacokinetics of pharmaceutical agents (or pharmaceutically acceptable salts, esters, and prodrugs thereof) which are metabolized by cytochrome P450 monoxygenase comprising coadministering ritonavir or a pharmaceutically acceptable salt, ester, and prodrug thereof.

BRIEF DESCRIPTION OF THE FIGURES

FIG. 1 shows the structures and chemical names of VX-950 and SCH 503034.

DETAILED DESCRIPTION OF THE INVENTION

Figure 2:
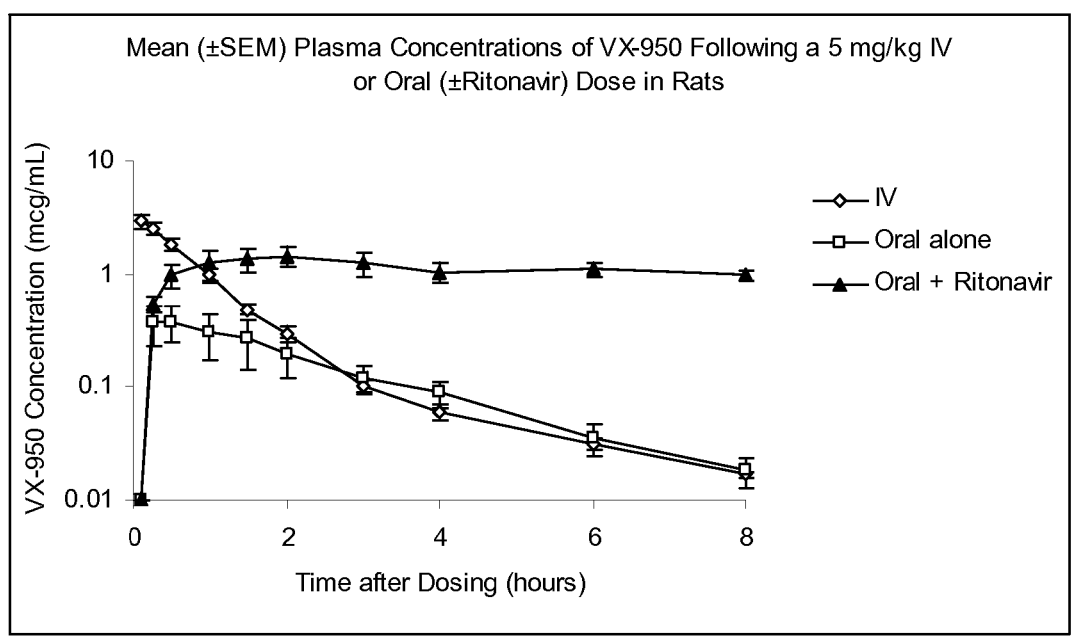
FIG. 2 shows enhancement of the plasma levels of VX-950 by coadministering with ritonavir in rats.

In accordance with the present invention, there is disclosed compositions and a method of improving the pharmacokinetics of pharmaceutical agents (or pharmaceutically acceptable salts, esters, and prodrugs thereof) which are metabolized by cytochrome P450 monoxygenase comprising coadministering ritonavir or a pharmaceutically acceptable salt, ester, and prodrug thereof.

"Coadministered" or "coadministering" means that the therapeutic agents can be formulated as separate compositions which are administered at the same time or different times, or alternatively that the therapeutic agents can be co-formulated and administered as a single composition.

Drugs which are metabolized by cytochrome P450 monoxygenase and which benefit from coadministration with ritonavir include 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid(1-cyclopropylaminooxalyl-butyl)-amide (VX-950), and 3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)-amide (SCH 503034).

In a preferred embodiment of the present invention, there is disclosed a composition wherein 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid (1-cyclopropylaminooxalyl-butyl)-amide (VX-950) is coadministered with ritonavir.

In another preferred embodiment of the present invention, there is disclosed a method for improving the pharmacokinetics of HCV compounds by coadministering 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid(1-cyclopropylaminooxalyl-butyl)-amide (VX-950), with ritonavir.

In another preferred embodiment of the present administration, there is disclosed a composition wherein 3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)-amide (SCH 503034) is coadministered with ritonavir.

In another preferred embodiment of the present administration, there is disclosed a method for improving the pharmacokinetics of HCV compound by coadmistering 3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)-amide (SCH 503034) and ritonavir.

In another preferred embodiment of the present invention, there is disclosed a method of inhibiting HCV in a mammal comprising coadministering 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid(1-cyclopropylaminooxalyl-butyl)-amide (VX-950), or a salt, ester, or prodrug thereof and ritonavir or a salt, ester, or prodrug thereof.

In another preferred embodiment of the present invention, there is disclosed a method of inhibiting HCV comprising coadministering 3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)- amide (SCH 503034) or a salt, ester, or prodrug thereof and ritonavir or a salt, ester, or prodrug thereof.

Ritonavir is (2S, 3S, 5S)-5-(N-(N-((N-methyl-N-((2-isopropyl-4-thiazoyl)methyl)amino)carbonyl)-L-valinyl) amino)-2-(N-((5-thiazoyl)methoxycarbonyl)amino)-1,6-diphenyl-3-hydroxyhexane. Ritonavir can be synthesized by the procedures described in PCT Patent Application No. WO94/14436, published Jul. 7, 1994, and U.S. Pat. No. 5,541,206 issued Jul. 30, 1996, both hereby fully incorporated by reference.

2-(2-{2-cyclohexyl-2[(pyrazine-2-carbonyl)-amino]-acetylamino}-3,3-dimethyl-butyryl)-octahydro-cyclopenta [c]pyrrole-1-carboxylic acid(1-cyclopropylaminooxalyl-butyl)-amide (VX-950), can be synthesized according to the procedures described in published PCT application WO02/18369, published Mar. 7, 2002, hereby fully incorporated by reference.

3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)-amide (SCH 503034), can be synthesized according to the procedures described in published patent application US 2003/0216325, having a publication date of Nov. 20, 2003, hereby fully incorporated by reference.

The compositions of the present invention are useful for treating HCV infections in mammals, particularly in humans. Accordingly, ritonavir can be coadministered with either VX-950 or SCH 503034 to treat HCV infection. Furthermore, the compositions of the present invention can also be coadministered with one or more anti-viral agents, including, but not limited to, entry inhibitors, protease inhibitors, polymerase inhibitors, and the like. In particular, the compositions of the present invention can be coadministered with anti-viral agents such as interferons and ribavirin. Examples of interferons suitable for use with ritonavir/VX 950 and ritonavir/SCH 503034 compositions of the present invention include, but are not limited to, interferon alpha-2a, interferon alpha-2b, pegylated interferon, pegylated interferon alpha-2a, pegylated interferon alpha-2b, concensus interferon alpha, pegylated concensus-inteferon alpha, interferon fused to a protein such as, but not limited to, interferon fused to serum human albumin (albuferon). The ritonavir/VX 950 and ritonavir/SCH 503034 compositions of the present invention can also be coadministered with other anti-viral agents. In a preferred embodiment, the ritonavir/VX 950 and ritonavir/SCH 503034 compositions of the present invention can be coadministered one or more pharmaceutical agents such as ribavirin and viramidine.

The following Examples are illustrative of the ability of ritonavir to improve the pharmacokinetics of aHCV compound.

EXAMPLE 1

Inhibition of the Metabolism of VX-950 and SCH 503034 in Human Liver Microsomes

Liquid handling was carried out on a Tecan EVO robotic system. Triplicate incubations were carried out at a final test compound concentration of 1 µM with 0.5 mg/ml microsomal protein, and 1 mM NADPH. Pooled human liver microsomes (1 mg/ml protein) and NADPH cofactor (2 mM) were prepared in 50 mM phosphate buffer at pH 7.4. Stock solutions (10 mM) of VX-950 or SCH 503034 were prepared in DMSO and then diluted to 100 µM in 1:1 acetonitrile/water. The solutions of compounds were added into the NADPH cofactor solution containing 0, 0.8 or 8 µM of ritonavir in a 2 ml 96-well plate. The resulting solution was added to the microsomes (1:1) that had been pre-incubated for 10 minutes at 37° C. Samples (0.1 ml) were incubated in 96-well plates at 37° C. for 0, 10, 20 and 30 min in a Tecan 4-slot incubator. At each time point, the robotic arm removed one of the replicate plates and the reactions were stopped by adding 1 volume (100 µl) of acetonitrile with internal standard (0.05 µM buspirone) to each well. All plates were centrifuged at 3500 rpm for 30 min, and the supernatant was transferred to a 96-well injection plate. The plates were stored at 4° C. until analyzed.

LC-MS/MS analysis: The samples were analyzed in positive mode using the turbospray ion source of PE/Sciex API 4000 Q-Trap mass spectrometer with Shimadzu HPLC system. Samples were injected (5 µL) onto a Lancer C18 column (5 µm, 30×2.1 mm) from Analytical Sales and Services Inc. (Pompton Plains, N.J.) and separation occurred via a gradient: The flow rate was 0.5 mL/min; starting conditions of 7.5% B, 2.5% C, increasing to 30% B and 10% C at 0.4 min. The percentage of B and C were rapidly increased to 74 and 21%, respectively, over 0.5 min and held for 0.7 min, then decreased back to the initial conditions over 0.1 min, and held for 0.4 min, for a total run time of 2.5 min. Mobile phase A was 95/5 water/methanol (v/v) with 10 mM ammonium acetate and 60 µL/L acetic acid. Mobile phase B was methanol containing 10 mM ammonium acetate and 60 µL/L acetic acid. Mobile phase C was acetonitrile.

Using the above conditions, the presence of ritonavir inhibited the metabolism of VX-950 and SCH 503034 in the following manner:

Metabolism of VX-950 and SCH 503034 in Human Liver Microsomes in the Absence or Presence of Ritonavir

|  | Concentration of ritonavir (micromolar) | | |
|---|---|---|---|
|  | 0 | 0.4 | 4.0 |
|  | Percent of Compound Remaining at t = 30 minutes | | |
| VX-950 | 30 | 81 | 100 |
| SCH 503034 | 18 | 77 | 100 |
|  | Percent Inhibition of Metabolism by Ritonavir | | |
| VX-950 | 0 | 72 | 100 |
| SCH 503034 | 0 | 71 | 100 |

EXAMPLE 2

Inhibition of the Metabolism of VX-950 and SCH 503034 in Rat Liver Microsomes

Using the procedure of Example 1, but substituting rat liver microsomes for human liver microsomes, the presence of ritonavir inhibited the metabolism of VX-950 and SCH 503034 in the following manner:

Metabolism of VX-950 and SCH 503034 in Rat Liver Microsomes in the Absence or Presence of Ritonavir

|  | Concentration of ritonavir (micromolar) | | |
|---|---|---|---|
|  | 0 | 0.4 | 4.0 |
|  | Percent of Compound Remaining at t = 30 minutes | | |
| VX-950 | 25 | 71 | 100 |
| SCH 503034 | 62 | 100 | 100 |
|  | Percent Inhibition of Metabolism by Ritonavir | | |

-continued

| | Concentration of ritonavir (micromolar) | | |
|---|---|---|---|
| | 0 | 0.4 | 4.0 |
| VX-950 | 0 | 61 | 100 |
| SCH 503034 | 0 | 100 | 100 |

EXAMPLE 3

Enhancement of the Plasma Levels of VX-950 by Coadministering with Ritonavir in Rats The pharmacokinetic behavior of VX-950 was characterized following a single 5 mg/kg intravenous or oral dose in Sprague-Dawley derived rats (n=3 per group); an additional group of three rats received a 5 mg/kg oral dose of VX-950, coadministered with a 5 mg/kg oral dose of ritonavir. VX-950 (±ritonavir) was prepared as 5 mg/mL solution in a 10% DMSO: 90% PEG-400 vehicle for both oral (±ritonavir) and intravenous administration. The 1 mL/kg intravenous dose was administered as a slow bolus (~1 minutes) in a jugular vein of the rats under isoflurane anesthetic; the 1 ml/kg oral dose (±ritonavir) was administered by gavage. Serial blood samples were obtained from a tail vein of each animal 0.1 (IV only), 0.25, 0.5, 1, 1.5, 2, 3, 4, 6 and 8 hours after dosing. The heparinized samples were placed on ice immediately following collection. Plasma was separated by centrifugation and stored frozen for subsequent analysis.

Concentrations of parent drug (and ritonavir) were determined by HPLC-MS/MS following liquid-liquid extraction of the plasma samples. Analysis was performed on a Sciex API 2000™ Biomolecular Mass Analyzer using Turbo Ion Spray. Peak areas of the title compounds and internal standards were determined using the Sciex MacQuan™ software. Calibration curves were derived from peak area ratio (parent drug/internal standard) of the spiked plasma standards using least squares linear regression of the ratio versus the theoretical concentration. The maximum plasma concentration ($C_{max}$) and the time to reach the maximum plasma concentration ($T_{max}$) were read directly from the observed plasma concentration-time data. The plasma concentration data were submitted to multi-exponential curve fitting using WinNonlin. The area under the plasma concentration-time curve from 0 to t hours (last measurable plasma concentration time point) after dosing ($AUC_{0-t}$) was calculated using the linear trapezoidal rule for the plasma-time profiles. The residual area extrapolated to infinity, determined as the final measured plasma concentration ($C_t$) divided by the terminal elimination rate constant ($\beta$), was added to $AUC_{0-t}$ to produce the total area under the curve ($AUC_{0-\infty}$). The apparent total plasma clearance ($CL_p$) was calculated by dividing the administered dose by the $AUC_{0-\infty}$. The volume of distribution, $V_c$, was estimated by dividing the dose by the extrapolated plasma concentration at time zero ($C_0$). The volume of distribution at steady state, $V_{ss}$, was estimated as a product of the plasma clearance ($CL_p$) and the mean residence time (MRT); the terminal-phase volume of distribution, $V_\beta$, was derived from the plasma clearance value ($CL_p$) divided by the plasma elimination rate constant ($\beta$). The bioavailability was calculated as the dose-normalized $AUC_{0-\infty}$ from the oral dose divided by the corresponding value derived from an intravenous dose.

As shown in FIG. 2 and below, the following mean (±standard error) plasma levels were obtained, indicating that coadministering with ritonavir substantially elevated the plasma levels of VX-950:

The following mean (±SEM, n=3) pharmacokinetic parameters were obtained:

| Route | $t_{1/2}$ | $V_{ss}$ | $V_\beta$ | $CL_p$ | AUC |
|---|---|---|---|---|---|
| IV | 2.8 | 2.4 (0.6) | 8.1 (2.6) | 1.7 (0.2) | 3.03 (0.33) |

| Route | $t_{1/2}$ | AUC | $C_{max}$ | $C_{8h}$ | $T_{max}$ | F |
|---|---|---|---|---|---|---|
| PO | 1.7 | 1.05 (0.33) | 0.43 (0.15) | 0.018 | 1.1 (0.5) | 34.8 (11.0) |
| PO+ | n.f. | 8.86 (1.62)* | 1.45 (0.29) | 0.973 | 1.8 (0.2) | >100 |

Mean (±SEM, n = 3); $t_{1/2}$ (hr); $V_c$ (L/kg); $V_\beta$ (L/kg); $CL_p$ (L/hr · kg); AUC (μg · hr/ml).
Mean (±SEM, n = 3); $t_{1/2}$ (hr); AUC (μg · hr/ml); $C_{max}$ (μg/ml); $T_{max}$ (hr); F (%); 2.0-8 hr AUC.
PO+ = oral solution dose of VX-950 + 5 mg/kg dose of ritonavir;
nf - unable to estimate plasma elimination half-life.

EXAMPLE 4

Figure 3:
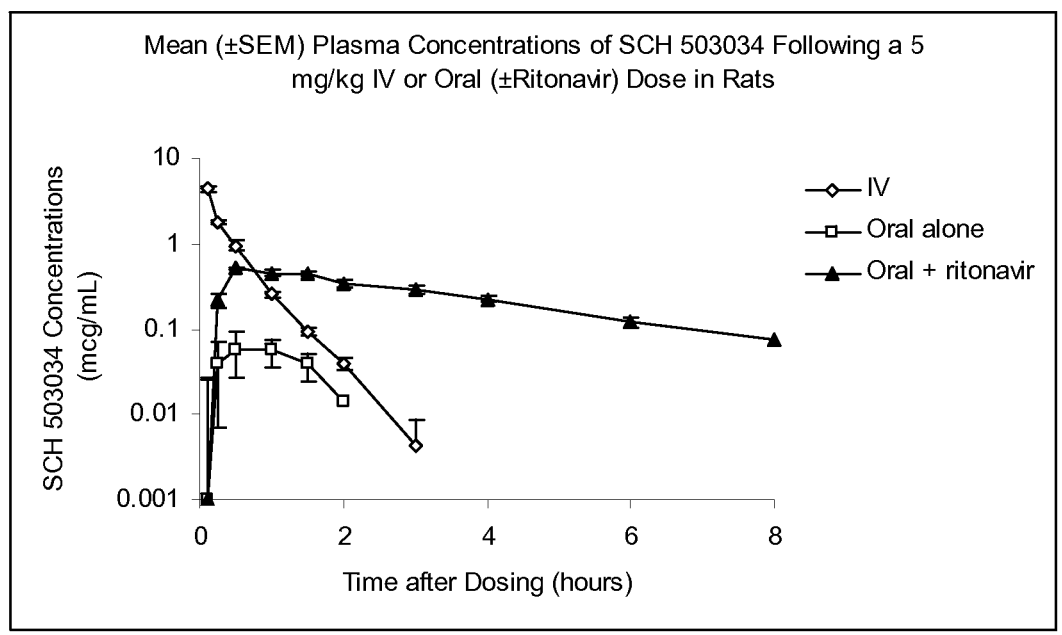
FIG. 3 shows enhancement of the plasma levels of SCH 503034 by coadministering with ritonavir in rats.

Enhancement of the Plasma Levels of SCH 503034 by Coadministering with Ritonavir in Rats Using the procedure of Example 3, but substituting SCH 503034 for VX-950, as shown in FIG. 3 and below, the following mean (±standard error) plasma levels were obtained, indicating that coadministering with ritonavir substantially elevated the plasma levels of SCH 503034:

The following mean (±SEM, n=3) pharmacokinetic parameters were obtained:

| Route | $t_{1/2}$ | $V_{ss}$ | $V_\beta$ | $CL_p$ | AUC |
|---|---|---|---|---|---|
| IV | 0.3 | 0.53 (0.23) | 0.92 (0.29) | 2.04 (0.62) | 3.12 (1.12) |

| Route | $t_{1/2}$ | AUC | $C_{max}$ | $C_{8h}$ | F |
|---|---|---|---|---|---|
| PO | n.f. | 0.11 (0.05) | 0.07 (0.02) | <0.001 | 3.5 (1.5) |
| PO+ | 2.5 | 2.18 (0.22)* | 0.52 (0.03) | 0.076 | 70.1 (7.0) |

Mean (±SEM, n = 3); $t_{1/2}$ (hr); $V_c$ (L/kg); $V_\beta$ (L/kg); $CL_p$ (L/hr · kg); AUC (μg · hr/ml).
Mean (±SEM, n = 3); $t_{1/2}$ (hr); AUC (μg · hr/ml); $C_{max}$ (μg/ml); F (%);
*0-8 hr AUC.
PO+ = oral solution dose of SCH 503034 + 5 mg/kg dose of ritonavir;
nf - unable to estimate plasma elimination half-life.

What is claimed:

1. A pharmaceutical coadministered composition comprising 3-[2-(3-tert-butyl-ureido)-3,3-diemthyl-butyryl]-6,6-dimethyl-3-aza-bicyclo[3.1.0]hexane-2-carboxylic acid (2-carbamoyl-1-cyclobutylmethyl-2-oxo-ethyl)-amide (SCH 503034) or a salt, ester, or ester thereof and ritonavir or a salt, ester, or ester thereof.

2. The method for improving the pharmacokinetics of 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid(1-cyclopropylaminooxalyl-butyl)-amide (VX-950), or a salt, ester, or ester thereof comprising coadministering 2-(2-{2-cyclohexyl-2[(pyrazine-2-carbonyl)-amino]-acetylamino}-3,3-dimethyl-yl-butyryl)-octahydro-cyclopenta[c]pyrrole-1-carboxylic acid(1-cyclopropylaminooxalyl-butyl)-amide (VX-950) or a salt, ester, or prodrug thereof with ritonavir or a salt, ester, or ester thereof.

3. The method for improving the pharmacokinetics of 3-[2-(3-tert-butyl-ureido)-3,3-diemthyl-butyryl]-6,6-dimethyl-3-aza-bicyc-lo[3.1.0]hexane-2-carboxylic acid (2-carbamoyl-1-cyclobutylmethyl-2-oxo-ethyl)-amide (SCH 503034) or a salt, ester, or ester thereof comprising coadministering 3-[2-(3-tert-butyl-ureido)-3,3-diemthyl-butyryl]-6,6-dimethyl-3-aza-bicyc-lo[3.1.0]hexane-2-carboxylic acid (2-carbamoyl- 1-cyclobutylmethyl-2-oxo-ethyl)-amide (SCH 503034) or a salt, ester, or prodrug thereof with ritonavir or a salt, ester, or ester thereof.

4. The composition of claim 1 coadministered with one or more pharmaceutical agents selected from the group consisting of interferon alpha-2a, interferon alpha-2b, pegylated interferon, pegylated interferon alpha-2a, pegylated interferon alpha-2b, concensus interferon alpha, pegylated concensus-inteferon alpha, interferon fused to a protein, ribavirin, and viramidine.

5. A pharmaceutical coadministered composition comprising 2-(2-{2-cyclohexyl-2[(pyrazine-2-carbonyl)-amino]-acetylamino}-3,3-dimethyl-butyryl)-octahydro-cyclopenta[c]pyrrole-1-carboxylic acid(1-cyclopropylaminooxalyl-butyl)-amide (VX-950) or a salt or ester thereof and ritonavir or a salt, ester, or prodrug thereof; wherein said composition is coadministered with one or more pharmaceutical agents selected from the group consisting of interferon alpha-2a, interferon alpha-2b, pegylated interferon, pegylated interferon alpha-2a, pegylated interferon alpha-2b, concensus interferon alpha, pegylated concensus-inteferon alpha, interferon fused to a protein, ribavirin, and viramidine.

\* \* \* \* \*